(12) United States Patent
Gutierrez-Rocca et al.

(10) Patent No.: US 6,524,615 B2
(45) Date of Patent: Feb. 25, 2003

(54) CONTROLLED RELEASE PHARMACEUTICAL COMPOSITION

(75) Inventors: Jose Gutierrez-Rocca, Miami, FL (US); Josephine Dunne, Plantation, FL (US); Saul A. Rios, Miramar, FL (US)

(73) Assignee: Kos Pharmaceuticals, Incorporated, Miami, FL (US)

( * ) Notice: Subject to any disclaimer, the term of this patent is extended or adjusted under 35 U.S.C. 154(b) by 0 days.

(21) Appl. No.: 09/790,239

(22) Filed: Feb. 21, 2001

(65) Prior Publication Data

US 2002/0160041 A1 Oct. 31, 2002

(51) Int. Cl.[7] .............. A61K 9/48; A61K 9/64; A61K 9/52; A61K 9/20; A61K 9/22
(52) U.S. Cl. ............ 424/451; 424/456; 424/457; 424/464; 424/465; 424/468; 424/484
(58) Field of Search ................... 424/451, 456, 424/484, 464, 465, 457, 468

(56) References Cited

U.S. PATENT DOCUMENTS

| | | | |
|---|---|---|---|
| 5,545,628 A | * | 8/1996 | Deboech et al. ............... 514/49 |
| 5,593,690 A | * | 1/1997 | Akiyama et al. ............ 424/457 |
| 5,977,158 A | * | 11/1999 | Rasmussen ................ 514/422 |
| 6,248,363 B1 | * | 6/2001 | Patel et al. ................. 424/497 |
| 6,294,195 B1 | * | 9/2001 | Oshlack et al. ............. 424/457 |

\* cited by examiner

*Primary Examiner*—Thurman K. Page
*Assistant Examiner*—S. Tran
(74) *Attorney, Agent, or Firm*—Frommer Lawrence & Haug LLP

(57) ABSTRACT

A sustained/prolonged release pharmaceutical dosage form is disclosed. The form comprises a hard shell capsule and a formulation comprising (a) a water insoluble medicament, (b) a high melting fatty ester, (c) a low viscosity oil, (d) a cellulosic polymer, and (e) a non-ionic surfactant.

32 Claims, 6 Drawing Sheets

CONTROLLED RELEASE PHARMACEUTICAL COMPOSITION

BACKGROUND OF THE INVENTION

One of the most frequently utilized methods to extend the duration of drug action in the body is by modification of the pharmaceutical dosage form. This is usually achieved with single or multicomponent matrix systems such as granules, pellets, tablets or a combination of the above where the drug delivery is mainly controlled by diffusion or erosion mechanisms.

Another commonly used procedure to sustain or control the rate of drug release is by utilizing polymer coating technology. Polymers with pH dependent or independent properties are coated onto the different dosage forms utilizing fluid bed or conventional coating equipment.

The delivery systems described above, traditionally have been used to manufacture many of the available pharmaceutical dosage forms in the market. However, for drugs that present a low melting point or are metastable at room temperature the only available solid oral unit dosage form has been the soft gelatin capsule.

Soft gelatin encapsulation is rather a complex process and usually requires the services of an outside contractor. However, many pharmaceutical companies would prefer to keep development activities in-house for reasons of confidentiality and control over the development process. With the new advances in pharmaceutical equipment technology it is now possible to formulate drug substances into semi-solid, liquid or paste-like form for filling into hard-shell two piece capsules. This type of formulation technology demonstrates an alternative for the difficult to manufacture soft gelatin technology and the ability to maintain the development activities in-house.

There are several advantages that can be obtained by formulating drugs in liquids and/or semisolid (molten) formulations to be filled into hard shell two piece capsules. These are the ability to formulate with low melting point materials, low-dosed or highly potent drugs, compounds that are oxygen- or moisture sensitive, and for drugs that require bioavailability enhancement.

Many of the liquid formulations in hard-shell capsules provide an immediate or fast release. This is usually achieved as a result of the immediate release of the contents due to the fast disintegration time of the gelatin at body temperature. Other formulations utilize sustained release liquid-filled release capsules utilizing thermosoftening matrices. The excipients most frequently utilized are the Gelucires®, Gattefosse®, France, since they are available as semisolids with a wide range of melting points and HLB values. This variety allows flexibility in mixing, adequate filling viscosity, different degrees of bioavailability enhancement and a sustained drug release from the semisolid matrix.

High melting glycerides have frequently been used as lubricants when formulating tablets or capsules. Lubricants have a great effect on the aspect of the finished product and the ejection of the tablet out of the die is improved. Lubricants are usually hydrophobic substances and when used in high amount can alter the desegregation time of the tablet thus delaying the bioavailability of the active ingredient.

The incorporation of lubricants (waxes, HMG) into tablet matrices has been a popular method to prolong drug release. For example, sustained release acetaminophen tablets with glyceryl behenate, Klucel HXF, hydroxy propyl cellulose (HPC), a swellable water-soluble polymer, and Carbopol® 934, a crosslinked polymer, has been prepared. It was observed that all tablets containing a sustained release agent exhibited some degree of prolonged drug release in vivo as compared to regular tablets. It was also noted that from all sustained release agents evaluated, glyceryl behenate provided the slowest release.

Glyceryl behenate as a potential controlled release wax matrix in spheres and tablets has been evaluated (10, 30 and 50%). At the 10% level no sustained action was observed. However, as the levels of glyceryl behenate increased a significant slower release of the drug was obtained. The results indicated that glyceryl behenate exhibited the potential to create a controlled release matrix.

Sustained release preparations have also been achieved from other high melting glycerides (glycerol palmitostearate and glyceryl monostearate). For example the release of theophylline embedded in a glycerol palmitostearate matrix containing varying amounts of mannitol and/or hydroxypropyl methyl cellulose 4000 (HPMC) was evaluated. The release of theophylline was modulated by varying the fraction of HPMC and/or mannitol used. When both HPMC and mannitol were used the matrix system developed followed a first-order dissolution release.

In general, natural, synthetic and/or semi-synthetic polymers such as cellulose or acrylics derivatives, have been used in high quantities (>10%) to retard the release of many pharmaceutical active ingredients. Such polymers are not usually recommended to be utilized in small quantities to retard the release of API.

SUMMARY OF THE INVENTION

A controlled release pharmaceutical formulation is disclosed. The formulation comprises a matrix construct of a component selected from a high melting point fatty acid ester, an oil, a polymeric cellulose derivative, and a mixture of any of the foregoing, having a selected medicament associated therewith.

BRIEF DESCRIPTION OF THE DRAWINGS

The accompanying drawing illustrates the invention. In such a drawing.

DETAILED DESCRIPTION OF THE INVENTION

Figure 1:
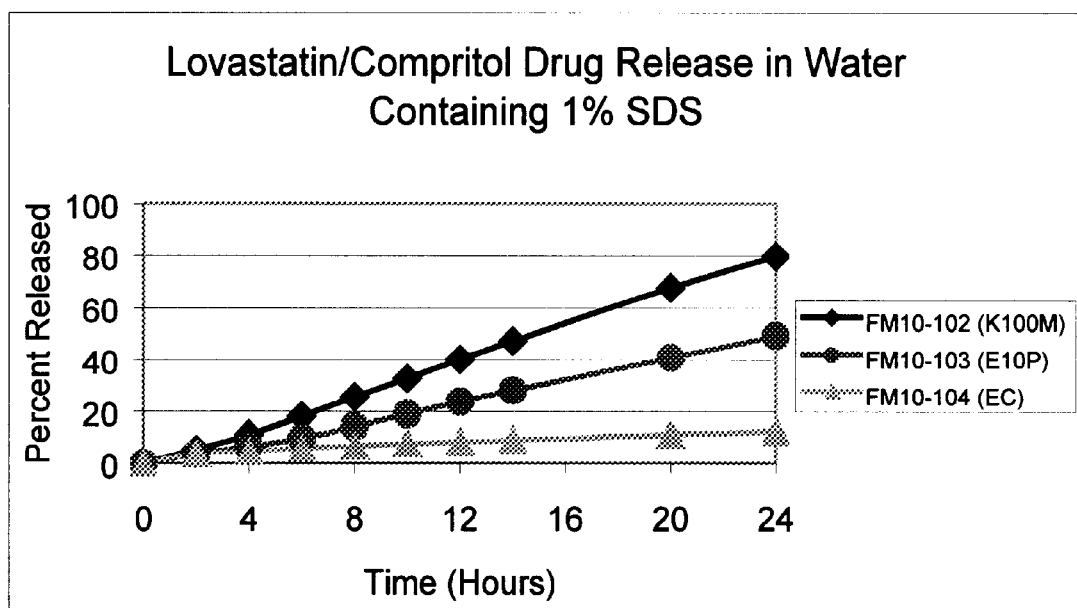
FIG. 1 is a graphical representation of the in vitro release of lovastatin using Compritol 888.

The present invention relates to a sustained or modulated pharmaceutical formulation comprising (1) a selected water insoluble medicament or drug, (2) a suitable construct with which the drug is associated, i.e. is encapsulated therewithin or being part of the construct. The construct provides a modulated release of the associated, e.g. encapsulated, drug to the body of a patient, e.g. a human being or another animal, when the construct is administered e.g. orally, to the patient.

As used herein the term "a water insoluble medicament, drug or active ingredient" includes such medicament drug or active ingredient that is (1) a sparingly soluble in water, i.e. 1 part solute into about 30 to about up to about 100 parts of water; (2) "slightly water soluble", i.e. 1 part of solute into about 100 to up to about 1,000 parts of water; (3) "a very slightly water soluble", i.e. 1 part of solute into about 1000 to up to about 10,000 parts of water; and (4) "practically water insoluble", i.e. 1 part of solute to at least about 10,000 parts of water; as defined in USP XXII.

The formulation is intended to be administered orally to the patient in a dosage form comprising a hard shell capsule filled with the formulation.

Suitable therapeutic medicament categories of drugs or medicaments are those which are water insoluble and include cardiovascular drugs, antiallergics, analgesics, bronchodilators, antihistamines, antitussives, antifungals, antivirals, antibiotics, other pain medicaments, antiinflamatories, etc. Particularly suitable medicaments include hydroxyzine pamoate; dihydropyridine calcium channel blockers, e.g. nifedipine, nimodipine, nisoldipine, nicardipine, amoldipine, etc.; statins e.g. atorvastatin, simvastatin, lovastatin, etc., anticonvulsants, e.g. phenytoin, carbamezepine, etc.; analgesics, e.g. ibuprofen, naproxen, indomethacin, etc. steroids, e.g. prednisone, prednisolone, hydrocortisone, etc.; fibrates, e.g. gemfibrozil, fenofibrate, clofibrate, etc.; vitamins, e.g. vitamins A, D, E and K, etc.

For purposes of the formulations of this invention, which are intended for incorporation into a hard shell capsule unit dosage form, the biotherapeutic medicament or drug is associated with the construct carrier with which it is destined to be combined. By "associate" or "associated" is meant that the water insoluble medicament is present as a matrix or a part of the matrix along with the component making up the construct or is encapsulated within the carrier matrix, or is on the surface of the carrier matrix.

A suitable construct is selected. Such a construct is one which will incorporate or encapsulate the selected medicament and provide a controlled or modulated release of the medicament therefrom to the sites of action or application to the patient's body, e.g. to the hepatobiliary receptors of the human being or other animal.

A suitable carrier construct comprises a material or component selected from the group comprising a high melting fatty acid ester, such as for example glyceryl behenate, gyceryl palmitosterate and glycerylstearate; low viscocity oils, e.g. vegetable oils, hydrogenated vegetable oils, corn oil, cottonseed oil, menhaden oil, safflower oil, sesame oil, shark-liver oil, soybean oil, olive oil and wheat germ oil; saturated, polyglycolyzed, glycerides, a cellulosic polymer, e.g. methocel E series, methocel A series, methocel K, series ethocel P series, low-substituted hydroxypropyl ether cellulose polymers, L H series methocel and a mixture of any of the foregoing.

A most preferred cellulosic polymer is a methylcellulose polymer having a structure,

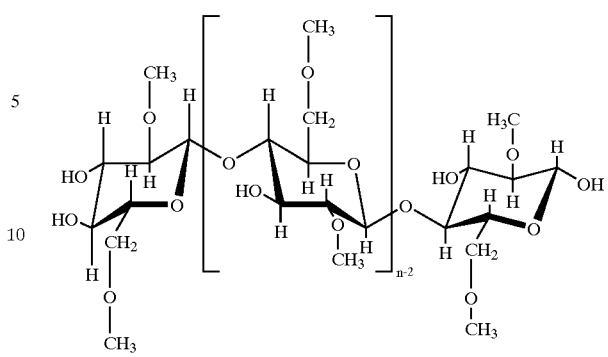

which are commercially available from the Dow Chemical Company, Midland, Mich., under the tradename "METHOCEL". e.g. METHOCEL A. Another most preferred cellulosic polymer is a hydroxypropoxyl methyl cellulose polymer having a structure,

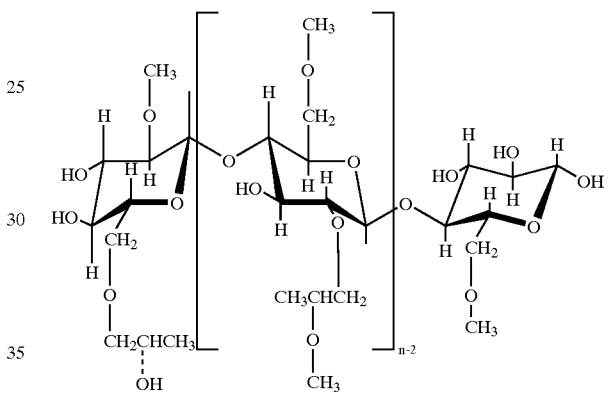

which are commercially available (Dow Chemical Company) under the designations METHOCEL E, METHOCEL F, METHOCEL and METHOCEL K brand products. Preferably, the formulation comprises a mixture of at least two of the foregoing components.

The dosage form comprising a hard shell capsule utilizes the formulation, i.e. the construct or the matrix having the medicament associated therewith. Preferably, the sustained/prolonged release pharmaceutical unit dosage form comprises the matrix or construct formulated from a mixture of the above-described materials or components.

The high melting fatty acid esters (high melting glycerides) of the formulation and the sustained/prolonged release capsule unit dosage forms of the present invention comprise esters of fatty acids and polyhydric alcohols, such as glycerol, melting at elevated temperatures within the range of from about 50° to about 80° C. The melting points of fatty acid esters of behenic acid (docosanoic acid), palmitostearic acid and stearic acid and glycerol fall within this range and are suitable for the formulations and unit dosage forms of the present invention. Other high melting fatty acid esters, that is, fatty acid esters melting within the range (about 50° to about 80° C.), may be employed in the formulations and dosage forms.

The oils of the formulations and the sustained/prolonged release capsule unit dosage forms of the present invention comprise triglycerides of fatty acids having short (12 to 14 carbon atoms), medium (16 to 18 carbon atoms) and long (18 to 22 carbon atoms) carbon chains and no, or up to 6 double bonds. Exemplary fatty acids are lauric acid (12 carbon atoms, no double bonds), myristic acid (14 carbon atoms, no double bonds), palmitic acid (16 carbon atoms, no double bonds), palmitoleic acid (16 carbon atoms, one double bond), stearic acid (18 carbon atoms, no double bonds), oleic acid (18 carbon atoms, 1 double bond), linoleic acid (18 carbon atoms, 2 double bonds), eicosapentaenoic acid (20 carbon atoms, 5 double bonds ("EPA") and docosahexanoic acid (22 carbon atoms, 6 double bonds), which are found in various animal and vegetable oils listed in the Table below.

Optionally, pharmaceutically acceptable excipients, compatible with the requirements for filling the capsules that the formulation be in the fluid state, i.e., a liquid or semi solid, at the filling temperature, may be included in the formulation. Such excipients comprise a surfactant, such as for example polysorbate 80; stabilizers/antioxidants, such as for example butylated hydroxytoluene, propyl gallate, vitamin E, ascorbic acid and ethylene diamine tetraacetic acid; solubilizers, such as for example N-methyl-2-pyrrolidone, citrate esters, e.g., Citroflex 2, acetylated monoglycerides,

TABLE

Super Refined ® Oils and the Associated Typical Fatty Acid Distribution (%)

| Super Refined Product | Myristic | Palmitic | Palmitoleic | Stearic | Oleic | Linoleic | Linolenic | EPA | DHA |
|---|---|---|---|---|---|---|---|---|---|
| Corn | 1 | 10 | 0 | 3 | 30 | 55 | 0 | 0 | 0 |
| Cotton-seed | 1 | 24.5 | 0 | 2.5 | 17 | 55 | <1 | 0 | 0 |
| Menhaden | 8.5 | 23 | 12.5 | 3 | 12.5 | 2 | <1 | 12 | 8.5 |
| Olive | 0 | 11.5 | 1 | 2 | 75 | 9.5 | 0 | 0 | 0 |
| Peanut | 0 | 7.5 | 1 | 4.5 | 62 | 20 | 0 | 0 | 0 |
| Safflower | 0 | 7 | 0 | 3 | 15 | 75 | 0 | 0 | 0 |
| Sesame | 0 | 8 | 0 | 4.5 | 43 | 41 | 0 | 0 | 0 |
| Shark-liver | 2 | 12 | 7 | 4 | 30 | 6 | 5 | 4 | 4 |
| Soybean | 0 | 9 | 0 | 4 | 24 | 52 | 8 | 0 | 0 |
| Wheat-germ | 0 | 13.5 | 0 | 3.5 | 19 | 54.5 | 7 | 0 | 0 |

The cellulosic polymers of the formulations and sustained/prolonged release capsule unit dosage forms of the present invention comprise glucose polysaccharide ethers having multiple glucose units and methyl, ethyl, hydroxyethyl, hydroxypropyl or hydropropyl methyl substitution. Exemplary cellulosic polymers having methylether substitution are the Methocels, i.e., methocel E10, methocel A4M, methocel K15M, methocel K100LV and methocel K100M, and the Ethocels, for example, ethocel P20 and low-substituted hydroxypropyl ether cellulose polymers LH11, LH22 and LH30.

Surfactants which may optionally be employed with the formulations and sustained/prolonged release capsule unit dosage forms of the present invention, comprise polysorbates, such as ethers of polyoxyethylene sorbitan and fatty acids. Exemplary surfactants are polysorbate 80 and polyoxyethylene 20 sorbitan monoleate, polyoxyxethylene alkyl ethers of the Brij- or Volpo series, Cremophor RH, Cremophor EL, polyoxyethylene sorbitan fatty acid esters of the Tween- or Crillet series, polyoxyethylene stearates of the Cerosynt- or Myrj series, lecithin, poloxamers, d-2-tocophenyl polyethylene glycol 1000 succinate (Vitamin E TPGS) and saturated polyglycolized glycerides (Labrasol, Labrafil and Gelucires),polyoxyethylene castor oil derivations, such as polysorbate 80 which is preferred.

The release of the insoluble or partially water soluble active ingredient or drug of the pharmaceutical unit dosage forms of the present invention is sustained over a prolonged period of about 24 hours. The sustained release of the water insoluble medicament from a hard shell capsule is dependent upon the type and amount of medicament, the high melting fatty acid ester, cellulose polymer and a surfactant (if employed).

The most preferred formulation comprises a water insoluble medicament, and a mixture comprising glyceryl behenate as the fatty acid ester, an oil, a cellulosic polymer, such as for example, a methyl or ethyl ether of a cellulose, e.g., a methocel or an ethocel, and polysorbate 80 surfactant.

e.g., Triacetin and Mygliols; viscosity modifiers, such as for example polyethylene glycols, e.g. PEG, and silica derivatives, e.g., silicon dioxide; and fillers such as for example hydrocarbons, e.g., paraffin and mineral oil. Preferably, combined with the component or components of the carrier and the drug is a surfactant, such as polysorbate 80.

The release of water insoluble medicaments from the unit dosage formulation generally depends on the type and amount of the high melting fatty acid in the formulation and varies substantially with the type and amount thereof. For example, the release of lovastatin from a formulation containing the same cellulose (methocel) component over a prolonged period of about 24 hours, is fastest with Precirol AT05, slowest with Compritol 888. The release of Lovastatin/Ethocel from a formulation of the precirol is moderately faster as the same formula containing compritol and ethocel.

The release of water insoluble medicament from a unit dosage formulation is markedly dependent on the type and amount of the cellulosic polymer. For example, lovastatin, compritol, is released considerably faster from a formulation of Methocel K100M than Ethocel P20. Similarly, lovastatin/precirol is released from a unit dosage formulation faster when the formulation contains Methocel K100M than Ethocel P20.

The formulations of the water insoluble medicaments of the present invention are useful for encapsulation in hard shell capsules for oral administration for the treatment of various diseases and disorders, for example, lovastatin, as an antilipidimic, or nifedipine as an antihypertensive agent, hydroxyzine pamoate as a antihistamine. The drugs are readily available from commercial suppliers.

The high melting fatty acid esters, the oils, the cellulosic polymers and surfactants and other excipients of the formulations of the present invention suitable for encapsulation in hard shell capsules are generally available from commercial sources. The water insoluble medicaments are also commercially available. Pharmaceutically acceptable acids and bases required for salt formation of water insoluble medicaments are available from suppliers such as Aldrich Chemical Company, Milwaukee, Wis.

The sustained/prolonged release pharmaceutical unit dosage forms are prepared by fluidizing matrix carrier material or components, e.g. a high melting fatty acid ester, an oil, a cellulosic polymer or a mixture of the foregoing, to provide a formulation, to which is added the medicament which dissolves therein, which is then filled into a hard shell capsule, while in the fluid state, and, generally, allowed to solidify in the capsule. The filling of the hard shell capsule is conveniently performed by a capsule filling machine for liquid filling of the type available, for example, from Robert Bosch GmbH, (Hofligen and Kars GKF/L Series), Germany, Harro Hoefleger GmbH, (KFM/L Series), Germany, or Zanasi Nigris SpA (AZ 20/L Series), Italy. The hard shell capsules are generally sealed by one of several methods. The filled capsule may be sprayed with a water alcohol mixture to seal the cap to the body of the container. Alternatively, the cap may be sealed to the body of the container by a bonding process, which entails passing the cap over a revolving wheel immersed in a water gelatin or a cellulose bath and then passing the capsule through a drying chamber to seal the gap between the cap and the body of the capsule with dried gelatin or cellulose. The bonding is generally performed on commercially available machines manufactured by Robert Bosch GmbH and Zanasi Nigris SpA, makers of capsule filling machines.

Empty hard shell capsules are commercially available from the Capsugel Division of Warner-Lambert Co., Greenwood, S.C., and from Shionogi Qualicaps, Whitsett, N.C., in various sizes to accommodate the dosage requirements for the treatment of disease or disorder states. For example, size 0 may be employed for unit dosage forms for potent drug formulations whereas size 000 would be required for a less potent drug, depending on the amounts of the components of the formulation and excipients.

Gelatin and hydroxypropylmethylcellulose (HPMC) capsules may be used as containers for the formulations. Hydroxypropylmethylcellulose capsules are preferred.

The following examples are illustrative and do not define the scope of the invention described and claimed herein.

EXAMPLES

General Example

The sustained/prolonged release formulations of the present invention are generally prepared by heating the matrix component or components until liquid (a melt), usually at the capsule filling temperature (70–90° C.) and adding the water insoluble medicament to the melt. The amount of water insoluble medicament utilized in all formulations is about 20% of the total amount of the formulation. Size #0 Hard-Shell hydroxypropylmethylcellulose capsules are utilized since they are heat resistant. In order to assure proper mixing and to reduce the amount of air entrapped with stirring (vortex created), batches containing a minimum of 50 grams are prepared. A general formulation is illustrated below.

| Ingredients | % | Qty (g) |
|---|---|---|
| Medicament | 20.0 | 10.00 |
| High Melting Glyceride | 25.0 | 12.50 |
| Surfactant | 1.0 | 0.50 |
| Cellulose Polymer | 3.0 | 1.50 |
| Vegetable oi | 51.0 | 25.50 |
| Total | 100.0 | 50.00 |

Example 1

Soybean oil, polysorbate 80, and Compritol 888 in the amounts shown in Table 1 were weighed and placed in a glass beaker. The mixture was heated to 75–80° C. until the contents melted by immersing the beaker into a water bath heated by a Hot-Plate. The melt in the amount shown in Table 1 below was stirred with a laboratory mixer fitted with a straight blade propeller to disperse the ingredients and create an homogeneous melt. To the melt, Methocel E or Ethocel 10P was slowly added with heating and stirring. After addition of the Methocel E 10P was complete, the melt was cooled to approximately 70° C., and then cooled at approximately 70° C., the water insoluble medicament lovastatin, was slowly added, and the melt was stirred until uniform. Capsules size 0 were filled with 500 mg of melt, with a pipette. The filling weights of each capsule were recorded to guarantee consistency. The melt was all regular type maintained at approximately 70° C. during the filling process. The release of the medicament, lovastatin, was then determined.

The dissolution release of the formulations was determined by the USP Basket Method (Apparatus 1). By this method, samples are tested in a 40 mesh basket rotating at 100 RPM. Release media were used in a volume of 900 Ml per dissolution vessel, maintained at 37° C. Double distilled deionized water with 1% sodium dodecyl sulfate was generally used as the dissolution media. Nine samples of 3.0 ml each were automatically collected at 2, 4, 6, 8, 10, 12, 14, 20 and 24 hours. The absorbency of the samples was measured at the peak wavelength in the ultraviolet spectrum with Hewllet Packard model 8453 spectrophotometer. The absorbency values were converted to percentages of added medicament that was released.

FIG. 1 shows the in vitro release of lovastatin using Compritol 888 and different cellulose products in the capsule system. The Methocel products differ in their chemical substitution attached to its cellulose backbone. The chemical substituents are hydroxypropoxyl and methoxyl groups. The methoxyl substituent provides more hydrophobicity and does not contribute to a great extent to the hydrophilic nature of the cellulose polymer thus having minimal influence on the rate of polymer hydration. On the other hand, the more hydrophilic hydroxypropoxyl group does contribute greatly to the rate of polymer hydration. Consequently, Methocel K products have the fastest rate of hydration than the other polymers due to its higher amount of the hydroxypropoxyl groups and a lower amount of the hydrophobic methoxyl group. Methocel E has a higher content of methoxyl group than hydroxypropoxyl groups attached thus providing a slower rate of hydration. Ethocel is a water insoluble polymer, with the same cellulose backbone and no water hydrating properties. The polymer is only organosoluble. The results show that for all formulas evaluated a sustained release of the drug was obtained. The fastest hydrating polymers provided a faster release thus allowing modulation of the sustained release effect. (Methocel K>Methocel E>Ethocel).

TABLE 1

| Formula/Ingredients | 1 | 2 | 3 |
|---|---|---|---|
| Lovastatin | 20.0 | 20.0 | 20.0 |
| Compritol 888 | 25.0 | 25.0 | 25.0 |
| Methocel E10P | 3.0 | | |
| Methocel K100M | | 3.0 | |
| Ethocel P20 | | | 3.0 |
| Olive Oil | 51.0 | 51.0 | 51.0 |
| Polysorbate 80 | 1.0 | 1.0 | 1.0 |

Example 2

Following the procedure of Example 1, using the amounts of the components shown in Table 2 below, hard shell capsules of the formulations were obtained. The release of the medicament was determined by the procedure of Example 1, and the results are recorded graphically in FIG. 2.

Figure 2:
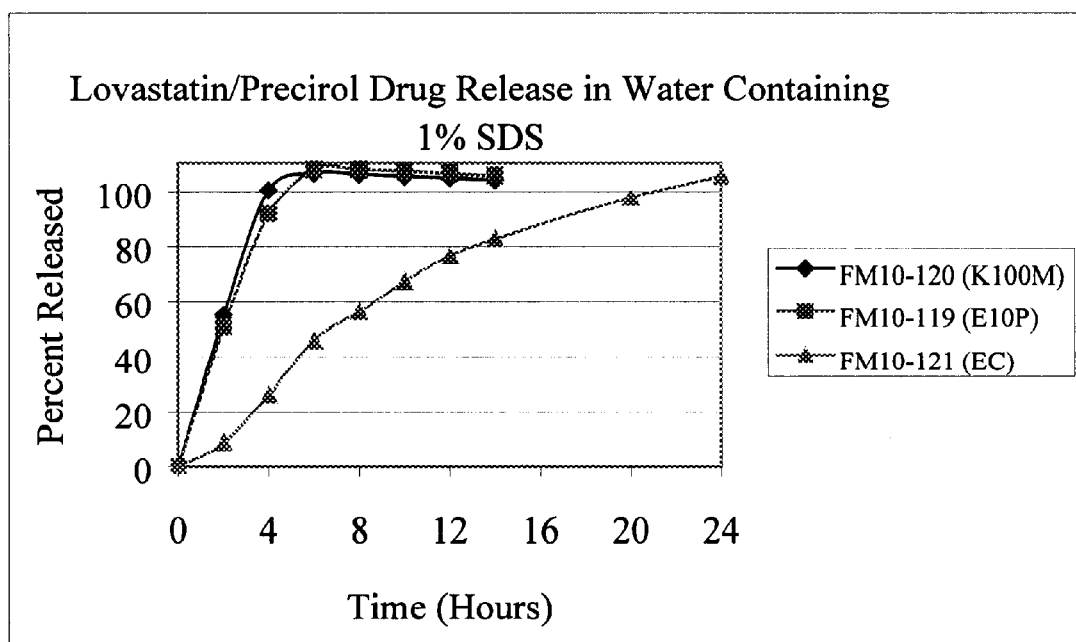
FIG. 2 is a graphical representation of the in vitro release of lovastatin using Precirol ATO5.

FIG. 2 shows the in vitro release of lovastatin using Precirol ATO5 and different cellulose based products in the capsule system. Precirol ATO5 has a lower melting point than Compritol 888 due to shorter fatty acid chains. Compritol 888 which is glyceryl behenate contains a 22 carbon fatty acid length chain. Precirol ATO5 is an equal mixture of the palmitate and sterate, 16 and 18 carbon units respectively. The use of a lower melting glyceride resulted in faster dissolution profiles of the water insoluble lovastatin. For systems containing the fast hydrating Methocel polymers, lovastatin was completely released in 4 hours. For systems containing the non-hydrating Ethocel a sustained release of the lovastatin was obtained over 24 hours. It is clearly demonstrated that the dissolution release is dependent on the type of polymer used.

TABLE 2

| Formula/Ingredients | 1 | 2 | 3 |
|---|---|---|---|
| Lovastatin | 20.0 | 20.0 | 20.0 |
| Precirol ATO 5 | 25.0 | 25.0 | 25.0 |
| Methocel E10 P | 3.0 | | |
| Methocel K100M | | 3.0 | |
| Ethocel | | | 3.0 |
| Olive Oil | 51.0 | 51.0 | 51.0 |
| Polysorbate 80 | 1.0 | 1.0 | 1.0 |

Example 3

This example illustrates the release of the active pharmaceutical ingredient hydroxyzine pamoate. In order to optimize the inclusion of this water insoluble salt in the capsule semisolid matrix, several surfactant classes and levels were evaluated (1–10% by weight). At levels lower than 2% by weight significant sample to sample variabilities were observed in the dissolution profiles indicating that the matrix was not well dispersed or a non-homogeneous mixture was obtained. Since excessive amounts of surfactant are not recommended for oral intake, the smallest amount which provides minimal sample to sample variability was evaluated (2% by weight level). These formulations listed in Table 3 below were prepared by melting the Compritol 888 with Labrasol and the specified surfactant in a suitable size beaker. The temperature of the mixture was kept at 75–80° C. with the aid of a heated plate and water bath. The mixture was constantly mixed until it became homogeneous. Once the mixture was homogeneous and free of any agglomerates, the cellulose polymer was added slowly to the melt with continuous mixing. The temperature of the mixture was then lowered to approximately 70° C. Once the mixture cooled to approximately 70° C., the hydroxyzine pamoate was slowly dispersed. The final melt was mixed well until uniform. Utilizing an appropriate pipette HPMC Capsules (#0) were filled with 500 mg of the melted mixture. The liquefied melt immediately solidified at room temperature. The actual filling weights were recorded for each capsule. Empty capsules were tared and balance zeroed. The melt mixture was maintained at approximately 70° C. during the filling operation.

Figure 3:
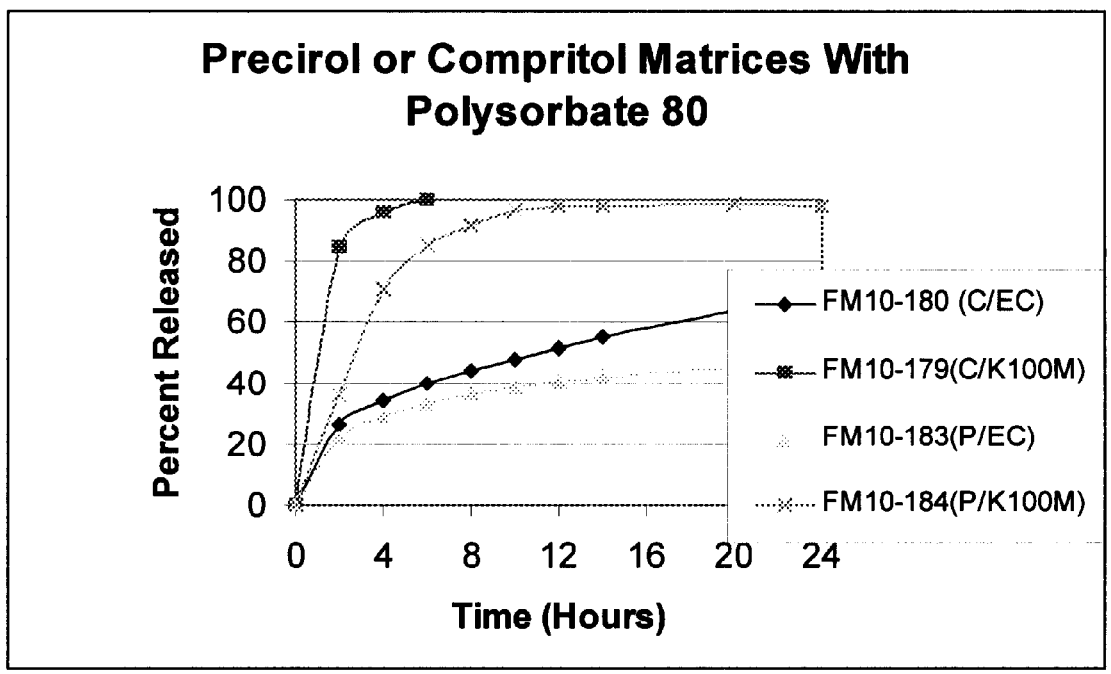
FIG. 3 is a graphical representation of the in vitro release of hydroxyzine pamoate using low HLB sufactant.
Figure 4:
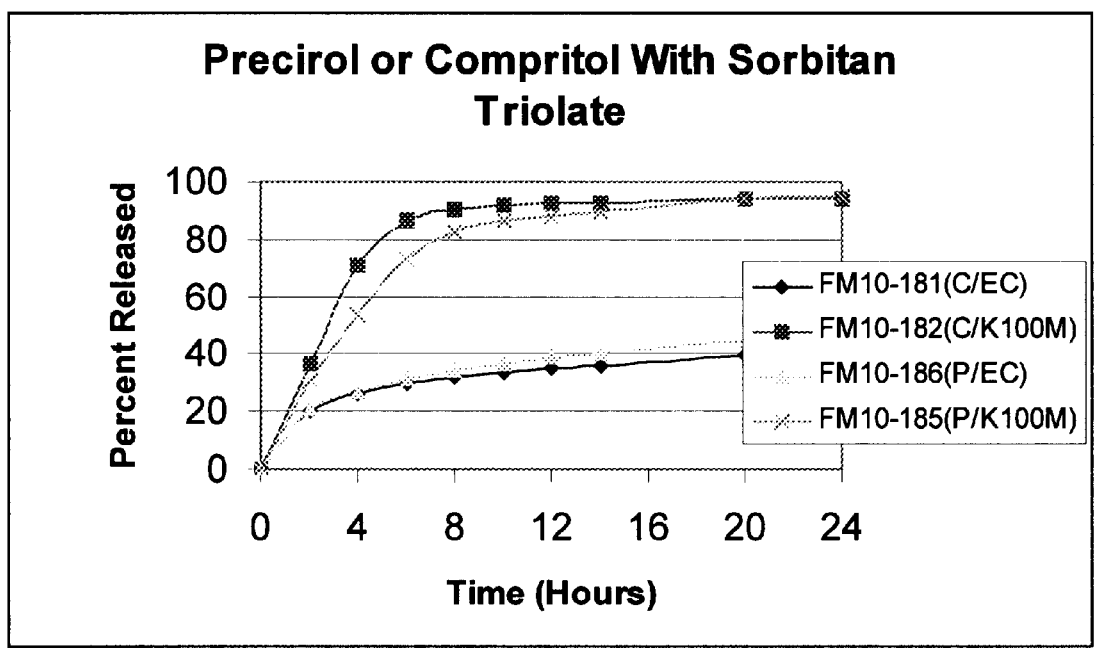
FIG. 4 is a graphical representation of the in vitro release of hydroxyzine pamoate using high HLB surfactant.

The results of combinations utilizing a low HLB surfactant are shown in FIG. 3. The results utilizing a high HLB surfactant are shown in FIG. 4.

Table 3

TABLE 3

| Formula/Ingredients | 1 | 2 | 3 | 4 |
|---|---|---|---|---|
| Hydroxyzine Pamoate | 20.0 | 20.0 | 20.0 | 20.0 |
| Compritol 888 | 25.0 | | | |
| Methocel K100 | 3.0 | | 3.0 | |
| Methocel E10 P | | | | |
| Ethocel | | 3.0 | | 3.0 |
| Precirol ATO 5 | | | 25.0 | |
| Labrasol | 51.0 | 51.0 | 51.0 | 51.0 |
| Polysorbate 80 | 2.0 | 2.0 | 2.0 | 2.0 |

Example 4

Figure 5:
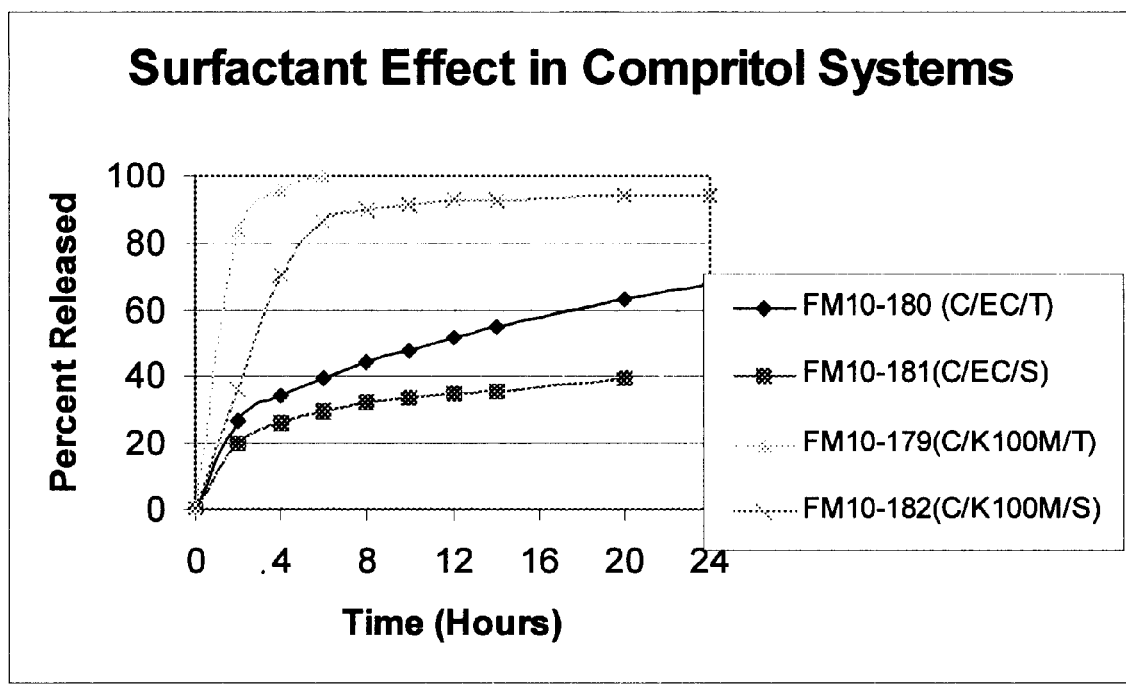
FIGS. 5 and 6 are graphical representations of the dissolution profiles of nifedipine.
Figure 6:
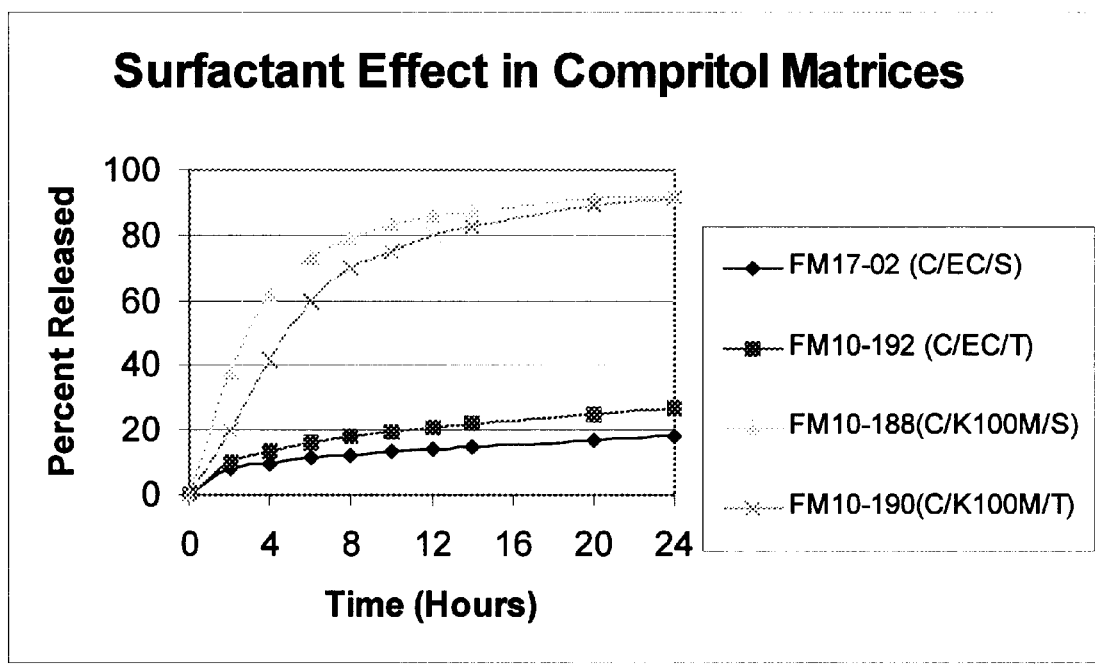

This example further illustrates the modulated sustained release behavior of nifedipine. Nifedipine is a calcium channel blocking agent indicated for the management of hypertension and other cardiovascular diseases. Extended release tablets are available at 60 and 90 mg doses. In order to adjust for the proper and recommended dosing, the filled weight of the capsules was reduced to 450 mg. At a 20% medicament level each capsule will contain a total of 90 mg nifedipine. The procedures used to manufacture the capsules were the same as those described in Example 1. The formulation and the percentages for each are described in Table 4—below. The dissolution profiles demonstrating the modulated sustained release effect of the capsule matrix and the effect of the polymer and surfactant combinations are seen in FIGS. 5 and 6.

TABLE 4

| Formula/Ingredients | 1 | 2 | 3 | 4 |
|---|---|---|---|---|
| Nifedipine | 20.0 | 20.0 | 20.0 | 20.0 |
| Compritol 888 | 25.0 | | | |
| Methocel K100 | 3.0 | | 3.0 | |
| Methocel E10 | | | | |
| Ethocel | | 3.0 | | 3.0 |
| Precirol ATO 5 | | | 25.0 | |
| Labrasol | 51.0 | 51.0 | 51.0 | 51.0 |
| Polysorbate 80 | 2.0 | 2.0 | 2.0 | 2.0 |

We claim:

1. A sustained/or prolonged release pharmaceutical unit dosage form comprising a hard shell capsule and a formulation comprising:

(a) a water insoluble medicament selected from the group consisting of hydroxyzine pamoate, nifedipine, nimodipine, nisoldipine, nicardipine, amlodipine, atorvastatin, simvastatin, lovastatin, genfibrozil, fenofibrate, and clofibrate;
(b) a high melting fatty acid ester selected from the group consisting of glyceryl behenate, glyceryl palmitostearate and glyceryl stearate;
(c) a low viscocity oil selected from the group consisting of corn oil, cottonseed oil, menhaden oil, safflower oil, sesame oil, shark-liver oil, soybean oil, olive oil and saturated polyglycolized glycerides;
(d) a cellulosic polymer selected from the group consisting of methocel A series, methocel E series, methocel K series, and ethocel P series; low-substituted hydroxypropyl ether cellulose polymers selected from the group consisting of LH11, LH22, and LH30; and
(e) a non-ionic surfactant selected from the group consisting of polysorbate 80, polyoxyethylene 20 sorbitan monoleate, polyoxyethylene alkyl ethers, polyoxyethylene sorbitan fatty acid esters, polyoxyethylene stearates, lecithin, poloxamers, d-2-tocophenyl polyethylene glycol 1000 succinate, and polyoxyethylene castor oil derivations.

2. A pharmaceutical unit dosage form according to claim 1 wherein the high melting fatty acid ester comprises from about 10% to about 50% by weight of the total weight of the formulation.

3. A pharmaceutical unit dosage form according to claim 2 wherein the high melting fatty acid ester comprises from about 15% to about 35% by weight of the total weight of the formulation.

4. A pharmaceutical unit dosage form according to claim 3 wherein the high melting fatty acid ester comprises about 25% by weight of the total weight of the formulation.

5. A pharmaceutical unit dosage form according to claim 1 wherein the oil comprises about 40% to about 60% by weight of the total weight of the formulation.

6. A pharmaceutical unit dosage form according to claim 5 wherein the oil comprises about 50% by weight of the total weight of the formulation.

7. A pharmaceutical unit dosage form according to claim 1 wherein the cellulosic polymer comprises from about 1% to about 5% by weight of the total weight of the formulation.

8. A pharmaceutical unit dosage form according to claim 7 wherein the cellulosic polymer comprises from about 3% by weight of the total weight of the formulation.

9. A pharmaceutical unit dosage form according to claim 1 wherein the surfactant comprises about 1.0% to about 10% by weight of the total weight of the formulation.

10. A pharmaceutical unit dosage form according to claim 9 wherein the surfactant comprises from about 2% by weight of the total weight of the formulation.

11. A pharmaceutical unit dosage form according to claim 1 wherein the high melting fatty acid ester comprises from about 10% to about 50% by weight, the oil comprises about 46% to about 61% by weight, the cellulosic polymer comprises from about 1% to about 5% by weight and the surfactant comprises from about 1.0% to about 10% of the total weight of the formulation.

12. A pharmaceutical unit dosage form according to claim 11 wherein the higher melting fatty acid ester comprises from about 15% to about 35% by weight of the total weight of the formulation.

13. A pharmaceutical unit dosage form according to claim 12 wherein the higher melting fatty acid ester comprises about 25% by weight, the oil comprises about 51% by weight, the cellulosic polymer comprises about 3% by weight, and the surfactant comprises about 1% of the total weight of the formulation.

14. A pharmaceutical unit dosage form according to claim 1 wherein the water insoluble medicament comprises about 20% by weight of the total weight of the formulation.

15. A pharmaceutical unit dosage form according to claim 1 wherein the high melting fatty acid ester comprises about 10% to about 50% by weight, the oil comprises from about 46% to about 61% by weight, the cellulosic polymer comprises from about 1% to about 5% by weight, and the surfactant comprises from about 1.0% to about 10% by weight, and the water insoluble medicament comprises about 20% by weight of the total weight of the formulation.

16. A pharmaceutical unit dosage form according to claim 15 wherein the high melting fatty acid ester comprises about 25% by weight, the oil comprises about 51% by weight, the cellulosic polymer comprises about 3% by weight, and the surfactant comprises about 2.0% and the water insoluble medicament comprises about 20% by weight of the total weight of the formulation.

17. A pharmaceutical formulation comprising a water insoluble medicament selected from the group consisting of hydroxyzine pamoate, nifedipine, nimodipine, nisoldipine, nicardipine, amlodipine, atorvastatin, simvastatin, lovastatin, genfibrozil, fenofibrate and clofibrate associated with,
(a) a high melting fatty acid ester selected from the group consisting of glyceryl behenate, glyceryl palmitostearate and glyceryl stearate;
(b) an oil selected from the group consisting of corn oil, cottonseed oil, menhaden oil, safflower oil, sesame oil, shark-liver oil, soybean oil, olive oil, wheat grain oil and a low viscocity polyglycolized glyceride;
(c) a cellulosic polymer selected from the group consisting of methocel E series, methocel A series, ethocel P series, methocel K series, low substituted hydroxypropyl ether cellulosic polymers, selected from the group consisting of LH11, LH22 and LH30; and
(d) a non-ionic surfactant selected from the group consisting of polysorbate 80, polyoxyethylene 20 sorbitan monoleate, polyoxyethylene alkyl ethers, polyoxyethylene sorbitan fatty acid esters, polyoxyethylene stearates, lecithin, poloxamers, d-2-tocophenyl polyethylene glycol 1000 succinate, and polyoxyethylene castor oil derivations.

18. A pharmaceutical unit dosage form according to claim 17 wherein the higher melting fatty acid ester comprises from about 10% to about 50% by weight of the total weight of the formulation.

19. A pharmaceutical formulation according to claim 18 wherein the high melting fatty acid ester comprises from about 15% to about 35% by weight of the total weight of the formulation.

20. A pharmaceutical formulation according to claim 19 wherein the high melting fatty acid ester comprises from about 25% by weight of the total weight of the formulation.

21. A pharmaceutical formulation according to claim 17 wherein the oil comprises about 46% to about 61% by weight of the total weight of the formulation.

22. A pharmaceutical formulation according to claim 21 wherein the oil comprises about 51% by weight of the total weight of the formulation.

23. A pharmaceutical formulation according to claim 17 wherein the cellulosic polymer comprises from about 1% to about 5% by weight of the total weight of the formulation.

24. A pharmaceutical formulation according to claim 23 wherein the cellulosic polymer comprises from about 3% by weight of the total weight of the formulation.

25. A pharmaceutical formulation according to claim 17 wherein the high melting fatty acid ester comprises from about 10% to about 50% by weight, the oil comprises about 46% to about 61% by weight, the cellulosic polymer comprises from about 1% to about 5% by weight and the surfactant comprises from about 1.0% by weight of the total weight of the formulation.

26. A pharmaceutical formulation according to claim 17 wherein the high melting fatty acid ester comprises about 25% by weight, the oil comprises about 51% by weight, the cellulosic polymer comprises about 3% by weight, and the surfactant comprises from about 1.0% by weight of the total weight of the formulation.

27. A process for the preparation of a sustained/prolonged release pharmaceutical unit dosage form comprising the steps of:
   (a) fluidizing a high melting fatty acid ester,
   (b) granulating the fluidized fatty acid ester, an oil, a cellulosic polymer, a surfactant and a water insoluble medicament;
   (c) transferring the fluidized granulate to a hard shell capsule wherein surfactant is selected from the group consisting of polysorbate 80, polyoxyethylene 20 sorbitan monoleate, polyoxyethylene alkyl ethers, polyoxyethylene sorbitan fatty acid esters, polyoxyethylene stearates, lecithin, poloxamers, d-2-tocophenyl polyethylene glycol 1000 succinate, and polyoxyethylene castor oil derivations; and water insoluble medicament is selected from the group consisting of hydroxyzine pamoate, nifedipine, nimodipine, nisoldipine, nicardipine, amlodipine, atorvastatin, simvastatin, lovastatin, genfibrozil, fenofibrate, and clofibrate.

28. A process according to claim 27 wherein the water insoluble medicament is selected from the group consisting of hydroxyzine pamoate, nifedipine, nimodipine, nisoldipine, nicardipine, amoldipine, atorvastatin, simvastatin, lovastatin, genfibrozil, fenofibrate and clofibrate.

29. A process according to claim 27 wherein the high melting fatty acid ester is fluidized at a temperature in the range of about 75° to 80° C.

30. The process according to claim 27 wherein the fluidized granulate is transferred to a hard shell capsule at a temperature of about 70° C.

31. A pharmaceutical unit dosage form according to claim 1 wherein the hard shell capsule comprises hydroxypropyl methylcellulose.

32. A process according to claim 27 wherein the hard shell capsule comprises hydroxypropyl methylcellulose.

* * * * *